US00PP08181P

United States Patent [19]

Saville

[11] Patent Number: Plant 8,181

[45] Date of Patent: Mar. 23, 1993

[54] MINIATURE ROSE PLANT NAMED SAVARS

[75] Inventor: F. Harmon Saville, Rowley, Mass.

[73] Assignee: Nor'East Miniature Roses, Inc., Rowley, Mass.

[21] Appl. No.: 740,582

[22] Filed: Aug. 5, 1991

[51] Int. Cl.[5] ..... A01H 5/00

[52] U.S. Cl. ..... Plt./7.1

[58] Field of Search ..... Plt. 7.1, 2

*Primary Examiner*—Howard J. Locker

*Attorney, Agent, or Firm*—Christie, Parker & Hale

[57] ABSTRACT

A new miniature rose with pink blend flowers of good form.

1 Drawing Sheet

SUMMARY OF THE INVENTION

The present invention relates to a new and distinct variety of rose plant of the miniature rose class, which was created by me by crossing as the seed parent the rose known as "High Spirits" (U.S. Plant Pat. No. 5,450) and as pollen parent the rose known as "Rainbows End" (U.S. Plant Pat. No. 5,482). The varietal denomination of this new rose is "Savars".

Among the novel characteristics possessed by this new variety which distinguishes it from its parent and all other varieties of which I am aware is its' attractive pink blend flowers of good exhibition form.

Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—"High Spirits".

*Pollen parent.*—"Rainbow's End".

Class: Miniature.

The following observations are made of specimens grown outdoors in Essex County, Mass., during the month of July.

Flower

Blooming habit: Continuous, recurrent.

A. Bud:

(1) *Size.*—Medium.

(2) *Form.*—Ovoid, pointed.

(3) *Color.*—As sepals divide, bud color is near 155A-D with near 55B-C to 52B at petal edge.

(4) *Sepals.*—Smooth, longer than bud.

(5) *Peduncle.*—Length — about ¾-inches. Aspect — straight. Strength — erect. Color — near 144B.

B. Bloom:

(1) *Size.*—Average size when fully expanded — about 1½ inches.

(2) *Borne.*—Singly, one to a stem, and several together in sprays of 3 to 5 blooms.

(3) *Form.*—High centered at first; outer petals loosely rool under; some inner petals have pointed apices; some outer petals have curved apices.

(4) *Petalage.*—Number of petals under normal conditions — about 50 to 55.

(5) *Color.*—After sepals fall and petals unfurl, predominant flower color of visible petal undersurface is near 155A-D flushed with pink at and near petal margins. Flowers retain the bicoloration of near white with pink edging as they open. Deeper hues may be seen where petals bunch but pink coloration washes into white areas of petals. As flowers unfurl, petal top surfaces display pink blend contrast with "silver", i.e., near white, reverse. Top petal surfaces are mixtures of pink tones, deeper at petal edges and margins, suffusing or washing into the near white coloration in the petals. Pink-to-white interface not distinct. At deepest tonality, at and near petal edge, coloration is near 55A to B, lightening to 55C to D. As flowers age, pink tones lighten to near 54C-D and eventually become near white with a pink hue. Contrasting bicoloration remins after three or more days, although the pink coloring lightens. General tonality from a distance is a pink blend bicolor. Color at point of petal attachment is near 4C.

C. Petals:

(1) *Texture.*—Average.

(2) *Appearance.*—Inside velvety and outside satiny.

(3) *Form.*—Wide fan shaped; some pointed apices.

(4) *Arrangement.*—Regularly arranged, imbricated.

(5) *Petaloids in center.*—Medium.

(6) *Persistence.*—Drop off cleanly.

(7) *Fragrance.*—Slight.

(8) *Lasting Quality.*—Very long lasting quality on plant and long lasting after cutting.

Reproductive Organs

A. Stamens, filaments and anthers:
*Arrangement and color.*—Regularly arranged around styles. Color — near 17D.

B. Pollen:
*Color.*—Near 16C.

C. Styles: Medium length.

D. Stigmas:
*Color.*—Near 156D.

E. Hips: Ovoid, $\frac{7}{8}'' \times \frac{5}{8}''$, orange color, seeds protrude Plant A. Form: Compact.

B. Growth: Vigorous, uniform branching.
*Height attained.*—About 15 to 18 inches.

C. Foliage: Compound 5 to 7 leaflets.
(1) *Size.*—Medium.
(2) *Quantity.*—Abundant.
(3) *Color.*—New foliage: Upper side — near 187A. Under side — near 185A. Old foliage: Upper side — near 137A. Under side — near 138A.
(4) *Shape.*—Oval, pointed.
(5) *Texture.*—Upper side is semi-glossy; under side is matte (6) *Edge.*—Serrate.
(7) *Serration.*—Regular.
(8) *Leaf stem.*—Color — near 147B. Under side — 146B.
(9) *Stipules.*—Medium length, slightly bearded
(10) *Resistance to Disease.*—Blackspot — Average. Mildew — Average. Rust — Average.

D. Wood:
(1) *New Wood.*—Color — near 138A. Bark — smooth.
(2) *Old wood.*—Color — near 144B. Bark — smooth.

E. Thorns:
(1) *Thorns.*—Quantity (main stalk) — few. On laterals from stalk — ordinary. Form — thin, pointed, curved downward. Length — about $\frac{3}{8}$-inch. Color — near 199D. Position — irregular.
(2) *Prickles.*—None.

F. Winter hardiness: Needs protection in severe climates.

I claim:

1. A new and distinct variety of rose plant of the miniature rose class, substantially as shown and described.

* * * * *

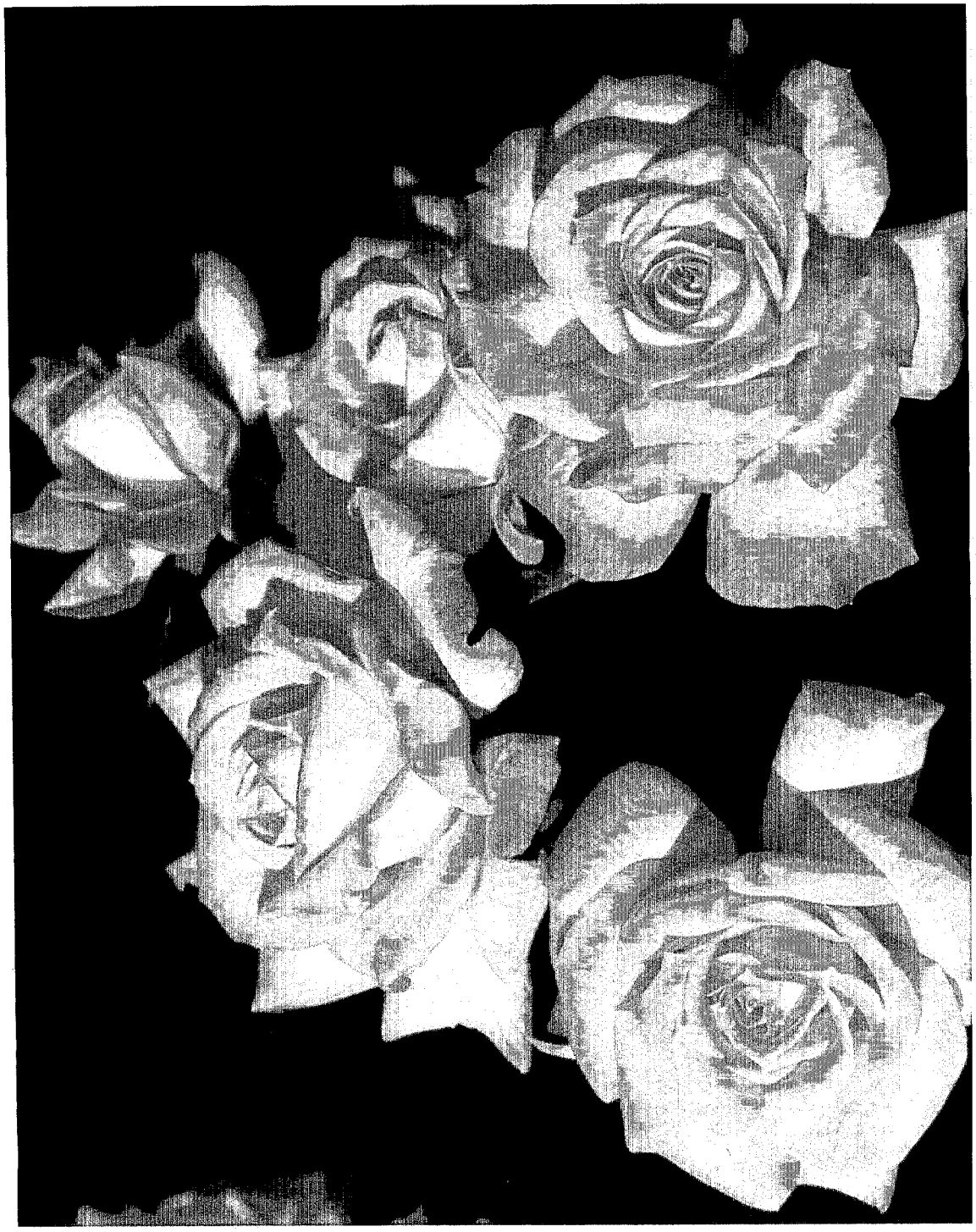

UNITED STATES PATENT AND TRADEMARK OFFICE

CERTIFICATE OF CORRECTION

PATENT NO. : Plant 8,181

DATED : March 23, 1993

INVENTOR(S) : F. Harmon Saville

It is certified that error appears in the above-identified patent and that said Letters Patent is hereby corrected as shown below:

Column 2, line 13, change "rool" to -- roll --.
Column 2, line 36, change "remins" to -- remains --.

Column 3, line 23, change "138A" to -- 138B --.

Signed and Sealed this

Twenty-first Day of June, 1994

*Attest:*

Bruce Lehman

BRUCE LEHMAN

*Attesting Officer*

*Commissioner of Patents and Trademarks*